US010342550B2

(12) United States Patent
Smith et al.

(10) Patent No.: US 10,342,550 B2
(45) Date of Patent: *Jul. 9, 2019

(54) DEVICE TO REDUCE SLOSH ENERGY ABSORPTION AND ITS DAMAGING EFFECTS THROUGH THE REDUCTION OF THE FLOW OF ONE OR MORE OUTFLOW VESSELS OF THE CRANIUM

(71) Applicants: TBI Innovations, LLC, Richmond, IN (US); Thornhill Research, Inc., Thornhill (CA)

(72) Inventors: David W. Smith, Richmond, IN (US); Joseph A. Fisher, Thornhill (CA)

(73) Assignee: TBI INNOVATIONS, LLC, Richmond, IN (US)

(*) Notice: Subject to any disclaimer, the term of this patent is extended or adjusted under 35 U.S.C. 154(b) by 642 days.

This patent is subject to a terminal disclaimer.

(21) Appl. No.: 14/861,582

(22) Filed: Sep. 22, 2015

(65) Prior Publication Data

US 2016/0008004 A1  Jan. 14, 2016

Related U.S. Application Data

(63) Continuation of application No. 12/931,415, filed on Feb. 1, 2011, now Pat. No. 9,168,045, which is a
(Continued)

(51) Int. Cl.
*A61B 17/132* (2006.01)
*A41D 13/05* (2006.01)
(Continued)

(52) U.S. Cl.
CPC ...... *A61B 17/1325* (2013.01); *A41D 13/0512* (2013.01); *A61B 17/12009* (2013.01);
(Continued)

(58) Field of Classification Search
CPC .... A61B 17/132–1355; A61F 5/30–34; A41D 13/0512; A61H 37/00; A61H 39/04; A61H 39/08–086
See application file for complete search history.

(56) References Cited

U.S. PATENT DOCUMENTS 2,271,927 A * 2/1942 Saighman .......... A61B 17/1322
128/DIG. 23
2,676,586 A * 4/1954 Coakwell, Jr. ..... A61B 17/1355
600/19
(Continued)

FOREIGN PATENT DOCUMENTS

CA  2823184 A1  4/2012
DE  3409335  9/1985
(Continued)

OTHER PUBLICATIONS

Leonard, A., et al., "Comparison of central venous and external jugular venous pressures during repair of proximal femoral fracture", British Journal of Anaesthesia (2008), vol. 101, No. 2, pp. 166-170.*
(Continued)

*Primary Examiner* — Elizabeth Houston
*Assistant Examiner* — Charles M Wei
(74) *Attorney, Agent, or Firm* — One LLP

(57) ABSTRACT

A first embodiment can be a device comprising a means to reduce SLOSH energy absorption in a fluid containing organism by reducing the flow of one or more outflow vessels of the cranium by compressing said vessels.

16 Claims, 2 Drawing Sheets

Figure 1:
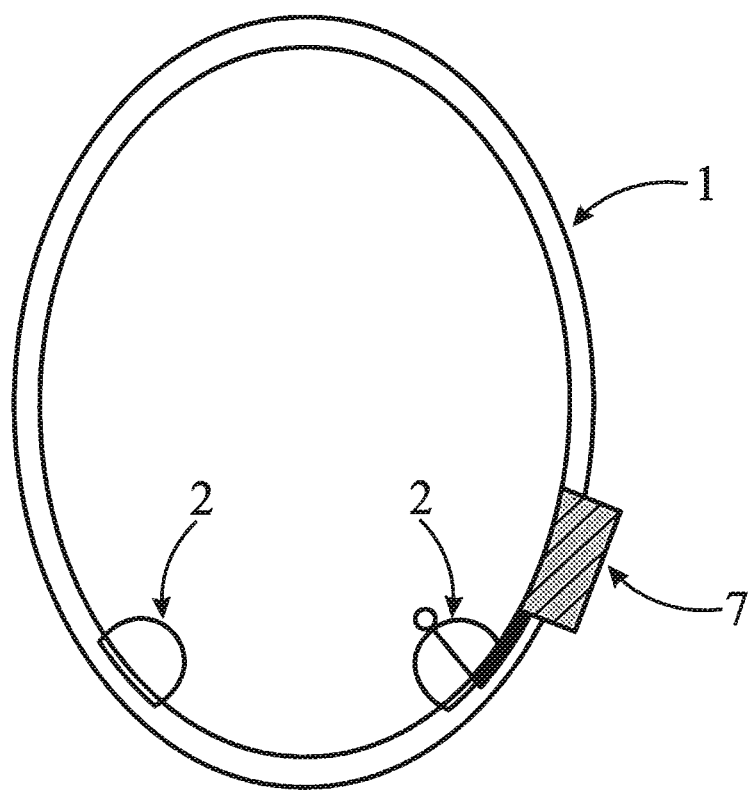

Related U.S. Application Data continuation-in-part of application No. 12/807,677, filed on Sep. 10, 2010, now Pat. No. 8,985,120.

(60) Provisional application No. 61/260,313, filed on Nov. 11, 2009, provisional application No. 61/241,625, filed on Sep. 11, 2009.

(51) Int. Cl.
| | | |
|---|---|---|
| *A61B 17/135* | (2006.01) | |
| *A61B 17/12* | (2006.01) | |
| *A41D 13/015* | (2006.01) | |
| *A61F 5/30* | (2006.01) | |
| *A61F 5/34* | (2006.01) | |
| *A41D 27/16* | (2006.01) | |
| *A41D 13/00* | (2006.01) | |

(52) U.S. Cl.
CPC ........ *A61B 17/135* (2013.01); *A41D 13/0015* (2013.01); *A41D 13/0156* (2013.01); *A41D 13/055* (2013.01); *A41D 13/0568* (2013.01); *A41D 13/0587* (2013.01); *A41D 27/16* (2013.01); *A41D 2400/14* (2013.01); *A41D 2600/10* (2013.01); *A61F 5/30* (2013.01); *A61F 5/34* (2013.01)

(56) References Cited

U.S. PATENT DOCUMENTS

| | | |
|---|---|---|
| 3,628,536 A | 12/1971 | Glesne |
| 3,765,412 A | 10/1973 | Ommaya et al. |
| 3,850,164 A | 11/1974 | Hare |
| 3,901,230 A | 8/1975 | Henkin |
| 4,188,946 A | 2/1980 | Watson |
| 4,343,303 A | 8/1982 | Williams |
| 4,628,926 A | 12/1986 | Duncan et al. |
| 4,817,595 A * | 4/1989 | Maass ............... A61F 13/00068 128/118.1 |
| 4,991,576 A | 2/1991 | Henkin et al. |
| 5,255,675 A | 10/1993 | Kolobow |
| 5,295,949 A | 3/1994 | Hathaway |
| 5,320,093 A | 6/1994 | Raemer |
| 5,338,290 A | 8/1994 | Aboud |
| 5,398,675 A | 3/1995 | Henkin et al. |
| 5,403,266 A | 4/1995 | Bragg et al. |
| 5,497,767 A | 3/1996 | Olsson et al. |
| 5,507,280 A | 4/1996 | Henkin et al. |
| 5,507,721 A | 4/1996 | Shippert |
| 5,584,853 A | 12/1996 | McEwen |
| 5,643,315 A | 7/1997 | Daneshvar |
| 5,776,123 A | 7/1998 | Goerg et al. |
| 5,957,128 A | 9/1999 | Hecker et al. |
| 6,007,503 A | 12/1999 | Berger et al. |
| 6,158,434 A | 12/2000 | Lugtigheid et al. |
| 6,165,105 A | 12/2000 | Boutellier et al. |
| 6,227,196 B1 | 5/2001 | Jaffe et al. |
| 6,245,024 B1 | 6/2001 | Montagnino et al. |
| 6,354,292 B1 | 3/2002 | Fisher |
| 6,558,407 B1 | 5/2003 | Ivanko et al. |
| 6,612,308 B2 | 9/2003 | Fisher et al. |
| 6,622,725 B1 | 9/2003 | Fisher et al. |
| 6,655,382 B1 | 12/2003 | Kolobow |
| 6,799,470 B2 | 10/2004 | Harada |
| 7,100,251 B2 | 9/2006 | Howell |
| 7,100,606 B2 | 9/2006 | Fisher et al. |
| 7,141,031 B2 | 11/2006 | Garth et al. |
| 8,381,362 B2 | 2/2013 | Hammerslag et al. |
| 8,985,120 B2 | 3/2015 | Smith |
| 2004/0127937 A1 | 7/2004 | Newton |
| 2005/0262618 A1 | 12/2005 | Musal |
| 2006/0095072 A1 | 5/2006 | TenBrink et al. |
| 2006/0200195 A1 | 9/2006 | Yang |
| 2007/0060949 A1 | 3/2007 | Curry et al. |
| 2007/0123796 A1 | 5/2007 | Lenhardt et al. |
| 2008/0021498 A1 | 1/2008 | Di Lustro |
| 2008/0154140 A1* | 6/2008 | Chang ............... A61B 5/02007 600/500 |
| 2009/0173340 A1 | 7/2009 | Lee |
| 2009/0209925 A1* | 8/2009 | Marinello ............. A61K 31/26 604/308 |
| 2010/0000548 A1* | 1/2010 | Haworth ................ A61F 5/055 128/845 |
| 2010/0071169 A1 | 3/2010 | Williams et al. |
| 2010/0294284 A1 | 11/2010 | Hohenhorst et al. |
| 2010/0318114 A1* | 12/2010 | Pranevicius .......... A61M 25/10 606/194 |
| 2011/0028934 A1* | 2/2011 | Buckman ............. A61B 17/135 604/385.12 |
| 2012/0197290 A1* | 8/2012 | Smith ................ A41D 13/0512 606/201 |
| 2013/0041303 A1 | 2/2013 | Hopman et al. |
| 2013/0333708 A1* | 12/2013 | Hassan ................... A61F 5/055 128/848 |
| 2014/0031787 A1 | 1/2014 | Razon-Domingo |
| 2014/0236221 A1* | 8/2014 | Zhadkevich ....... A61B 17/1325 606/202 |
| 2015/0313607 A1* | 11/2015 | Zhadkevich ....... A61B 17/1325 606/201 |
| 2016/0169630 A1* | 6/2016 | Augustine ................ F41H 1/00 2/468 |
| 2018/0325194 A1* | 11/2018 | Elvira ................ A61B 17/1325 |

FOREIGN PATENT DOCUMENTS

| | | |
|---|---|---|
| FR | 719 730 A | 2/1942 |
| WO | WO 98/46144 A1 | 10/1998 |
| WO | WO 2011/048518 A1 | 4/2011 |
| WO | WO 2012/054262 A1 | 4/2012 |
| WO | WO 2012/156335 A1 | 11/2012 |
| WO | WO 2012/168449 A1 | 12/2012 |
| WO | WO 2013/055409 A1 | 4/2013 |

OTHER PUBLICATIONS

EP, 12840429.0 Communication pursuant to Article 94(3), dated Mar. 24, 2017.
AU, Patent Examination Report No. 2, Patent Application No. 2011318427, dated Apr. 21, 2016.
CA, Office Action, Appln. No. 2,812,131, dated Dec. 6, 2013.
CA, Office Action, Appln. No. 2,812,131, dated Oct. 8, 2014.
CA, Office Action, Appln. No. 2,823,184, dated Dec. 11, 2013.
CA, Office Action, Appln. No. 2,823,184, dated Aug. 13, 2014.
CA, Office Action, Appln. No. 2,823,184, dated Oct. 29, 2014.
EP, Extended Search Report, Appln. No. 13166318.9, dated Sep. 3, 2013.
EP, Extended Search Report, Appln. No. 11 83 4865, dated Sep. 17, 2014.
NZ, Examination Report, Appln. No. 613566, dated Oct. 17, 2014.
U.S., Non-Final Office Action, U.S. Appl. No. 12/931,415, dated Mar. 13, 2013.
WO, International Search Report, Appln. No. PCT/US2014/028004, dated Sep. 11, 2014.
Batson, "Anatomical Problems Concerned in the Study of Cerebral Blood Flow", Federation Proceedings, Federation of American Societies for Experimental Biology, 1944, 139-144, vols. 3-4.
Cardoso et al., "Microplate Reader Analysis of Triatomine Saliva Effect on Erythrocyte Aggregation", Materials Research, Copyright 2007, 31-36, vol. 10, No. 1.
Ferguson et al., "Cerival collars: a potential risk to the head-injured patient", Injury: International Journal of Care of the Injured, 1993, 454-456, vol. 24, No. 7.
Finnie et al., "Animal Models—Traumatic Brain Injury", Veterinary Pathology, 2002, 679-689, vol. 39.
Gilland et al., "A Cinemyelographic Study of Cerebrospinal Fluid Dynamics", American Journal of Roentgenology, Jun. 1969, 369-375, vol. 106, No. 2.
Gregg et al., "Experimental Approaches to the Study of the Cerebral Circulation", Federation Proceedings, Federation of American Societies for Experimental Biology, 1944, 144-151, vols. 3-4.

(56) References Cited

OTHER PUBLICATIONS

Kitano et al., "The Elasticity of the Cranial Blood Pool", Journal of Nuclear Medicine, 1964, 613-625, vol. 5.
May et al., "Woodpecker Drilling Behavior, An Endorsement of the Rotational Theory of Impact Brain Injury", Arch Neurology, Jun. 1979, 370-373, vol. 36.
Moyer et al., "Effect of Increased Jugular Pressure on Cerebral Hemodynamic", Journal of Applied Physiology, Nov. 1954, 245-247, vol. 7, No. 3.
NHTSA, "Transportation Safety", Brain Injury Association of American, Apr. 2001, 2 pages.
Templer et al., "Preventable Brain Damage, Brian Vulnerability and Brain Health", Springer Publishing Company, Copyright 1992, 95-107.
Torres et al., "Changes in the Electroencephalogram and in Systemic Blood Pressure Associated with Carotid Compression", Neurology, Nov. 1970, 1077-1083, vol. 20, No. 11.
Tyrrell, "Observations on the C.S.F. Pressure During Compression of the Jugular Veins", Postgraduate Medical Journal, 1951, 294-295, vol. 27.
Vannucci et al., "Carbon dioxide protects the perinatal brain from hypoxic-ischemic damage: an experimental study in the immature rat", Department of Pediatrics (Pediatric Neurology), Jun. 1995, 868-874, vol. 95, No. 6.

\* cited by examiner

DEVICE TO REDUCE SLOSH ENERGY ABSORPTION AND ITS DAMAGING EFFECTS THROUGH THE REDUCTION OF THE FLOW OF ONE OR MORE OUTFLOW VESSELS OF THE CRANIUM

CROSS-REFERENCE TO RELATED APPLICATIONS

This patent application is a continuation of U.S. application Ser. No. 12/931,415, dated Feb. 1, 2011, which is a continuation-in-part of U.S. application Ser. No. 12/807, 677, filed Sep. 10, 2010, now U.S. Pat. No. 8,985,120, which claims priority to U.S. Provisional Application Nos. 61/260, 313 filed on Nov. 11, 2009, and 61/241,625, filed on Sep. 11, 2009, all of which are incorporated herein by reference.

DETAILED DESCRIPTION OF THE DRAWINGS

FIG. 1 illustrates one embodiment of the invention in which collar 1 of the invention having two inwardly directed protuberances 2 and device 7 which monitors and records information about the subject (e.g., heart rate). Optionally, device 7 also has an embedded transceiver and/or receiver to allow communication of that information.

Figure 2:
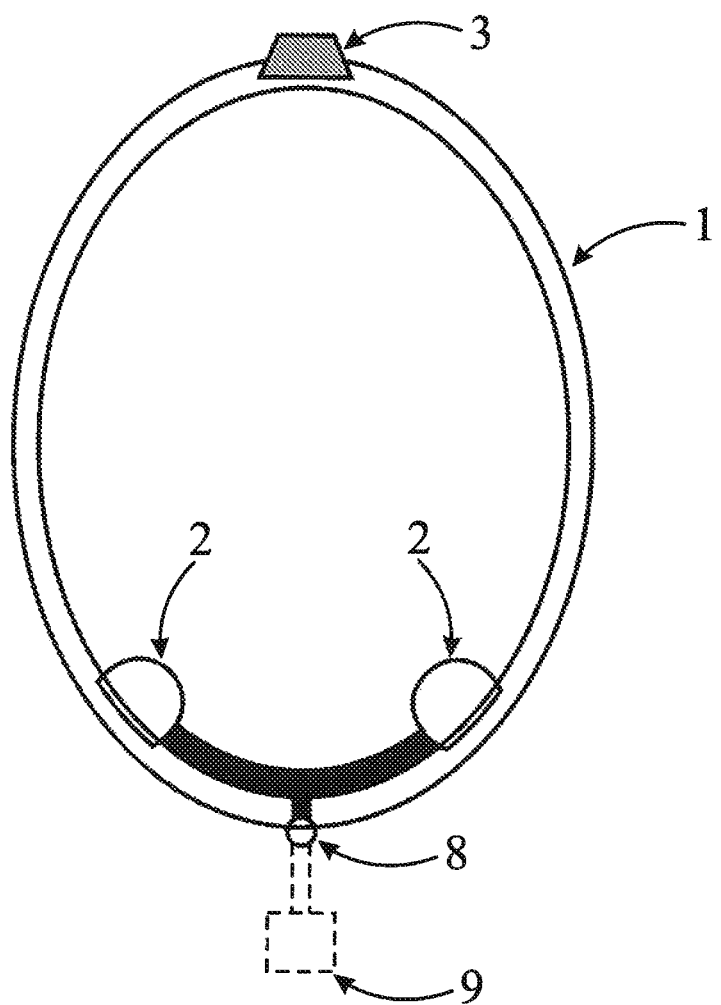

FIG. 2 illustrates anther embodiment of the invention in which the collar 1 of the invention having two inwardly directed protuberances 2 and a cinch 3, along with a removable manual pump 9 and pressure release valve 8 for inflating the protuberances 2, which are in fluid communication with each other and the pump 9.

DETAILED DESCRIPTION OF THE INVENTION

When liquid in a tank or vessel experiences dynamic acceleration or deceleration, there will develop, a variety of wave motions in the liquid. The oscillation of a fluid caused by external force, called sloshing, occurs in moving vessels containing liquid masses, such as trucks, aircraft, and liquid fueled rockets. This sloshing effect can be a severe problem in energy absorption, and thus, vehicle stability and control. Simply stated, the concept of this invention is to reduce slosh effects in living creatures.

The mitigation of blast wave and collision damage is based largely on the principle of energy absorption of fluid-filled containers. As there becomes more room for movement of fluid within a vessel, more energy can be absorbed (SLOSH) rather than transmitted through the vessel. To reduce this energy absorption, one must attempt to more closely approximate elastic collisions. Elastic collisions are those that result in no net transfer of energy, chiefly, acoustic, kinetic, vibrational, or thermal (also stated as a coefficient of restitution (r) approximating 1.0). Various embodiments described below may locally alter, elevate, or temporarily maintain an altered physiology of an organism to reduce the likelihood of energy absorption through SLOSH whereby the coefficient of restitution (r) is increased. The coefficient of restitution (r) indicates the variance of an impacting object away from being a complete total elastic collision (an (r) of 1.0=no energy transfer). Blast or energy absorption in an organism can be viewed as a collision of bodies and thus be defined by a transfer of energies through elastic or inelastic collisions. The mechanisms for biological fluids and molecules to absorb energy can thus be identified and the resultant means to mitigate that absorption can be achieved through several SLOSH reducing techniques. Dissipation of energies post blast is also potentiated through these techniques.

An effort to reduce the available space for movement of the brain by increasing cerebral blood volume can serve the purpose of mitigating Traumatic Brain Injury (TBI), red cell injury, or increasing orthostatic or G-tolerance through SLOSH mitigation at a cellular level (micro SLOSH) or organ level (macro SLOSH). Red blood cells (RBC) or erythrocytes are highly distensible and have a "sloshable" volume to surface area of only 60 percent. Distending or stiffening these erythrocytes can reduce SLOSH within the individual cells at a cellular (micro SLOSH) level and thus reduce energy absorption upon collision. Molecules themselves have a three dimensionality and can have a lack of cross-bridging providing for floppy conformational changes that can promote SLOSH. Several mechanisms disclosed can safely and reversibly alter the conformational state of certain structures, cells and molecules in the circulatory system that will then reduce energy absorption through SLOSH at a molecular (molecular SLOSH) level. Elevating the local $CO_2$ and hence lowering the pH environment of an organism can also serve to mitigate SLOSH.

Raised inspired $CO_2$ (hypercapnia) can mitigate TBI through the reduction of macro SLOSH inside the cranium, but also has the ability to reduce the micro SLOSH inside each individual RBC and reduce the molecular SLOSH of each individual hemoglobin molecule. Each of these physiology changes allows a better passage of imparted forces through the blood and brain tissues with less of the energy being absorbed. Within the brain's more than 150 cc of cerebral blood, there are more than 1,000,000,000,000 erythrocytes (1 trillion cells) that hypercapnia can potentiate to more closely approximate elastic collisions of cells thus reducing the blast or collision energy absorption. Further, a hypercapnic state can also potentiate the collisions of all the hemoglobin molecules present in the cranium and body to be more elastic, thus reducing blast or collision energy absorption. There are 80 trillion RBC in the human body, more than one trillion in the brain space at any one time. All of these cells are susceptible to SLOSH energy absorption, and that absorption would be reduced in the setting of hypercapnia. Further, there are 240 million molecules of hemoglobin inside each RBC. Consequently, there are thus $1.9 \times 10^{22}$ hemoglobin molecules which are able to absorb the energies of a blast. The SLOSH energy absorption of these molecules can be significantly reduced by hypercapnia altering the molecules to approximate more elastic collisions.

Hemoglobin is made up of four iron containing heme components and four globins that surround (pocket) each heme, and in essence waterproof these hemes. If the blast energies are absorbed by fluids and blood cells, they are preferentially absorbed by hemoglobin which is then conformationally altered to allow water to enter the heme-pocket leading to a rapid, catalytic oxidation to methemoglobin and superoxide. Superoxide is oxygen with an extra electron; methemoglobin is merely an oxyhemoglobin devoid of a superoxide. Without this extra electron, methemoglobin does not have the ability to carry or transfer oxygen (thus the brain suffocates), and in the case of blast lung, massive levels of methemoglobin have been recorded. The erythrocytes can slowly reduce methemoglobin back to functional hemoglobin but if this methemoglobin reductase reaction is not capable of diverting adequate electrons to counter this redox chemistry, spillover occurs into the oxidative damaging formation of superoxide, nitric oxide, peroxinitrite, etc. When an electron moves from one molecule to another, the donor molecule is thus oxidized while the receiving molecule is reduced (hence the term "redox"). For decades methylene blue has been used as the safe and well tolerated antidote for cyanide poisoning (and methemoglobinemias). It safely and dramatically facilitates the reductive pathways of methhemoglobin back into hemoglobin. Hypercapnia not only pushes methylene blue into erythrocytes where it can be functional, but it also appears to actually drive methemoglobin reductase to more quickly convert methemoglobin back to hemoglobin. Further, the anti-oxidants (electron donors) ascorbic acid (vitamin C) and riboflavin are also driven into the erythrocyte by hypercapnia; These antioxidants are not useful for post blast or energy absorption outside of erythrocytes. A soldier or athlete can be given physiologic daily doses of Vitamin C, Riboflavin and methylene blue (not a vitamin) and upon triggering a need, hypercapnia will drive these cofactors into the erythrocyte where they can mitigate the after effects of blast energy absorption.

A first embodiment is a method to reduce SLOSH energy absorption through reduction of inelastic collisions in a fluid containing organism wherein the method is one or more of reversibly increasing pressure, or volume within the organs or cells, or reversibly altering vascular, molecular, or cell wall stiffness or configuration within said organism. One embodiment of a method to increase the volume and/or pressure within the cranium can be by temporarily raising the $pCO_2$ in the body of the organism by way of altering the fractional percentage of $CO_2$ inspired by the organism or reducing its $CO_2$ elimination below that of $CO_2$ production by the body. Such a method can maintain the above hypercapnic inspired $CO_2$ levels to exceed baseline levels. The $CO_2$ is actively and instantly pumped into erythrocytes and after the external $CO_2$ delivery stops, the intracellular $CO_2$ levels may take hours to return to normal. These levels can be achieved and maintained by an externally imparted respiratory circuit which can modulate the fractional percentage of $CO_2$ inspired by the organism or reduce the rate of $CO_2$ elimination below that of $CO_2$ production by the body. The circuit could be one or more of a non-breathing circuit, a breathing circuit mask, or a breathing circuit capable of organizing exhaled gas so as to modulate the fractional percentage of $CO_2$ inspired by the organism (a range from 0.05 to 100% could be utilized) or net reduction of CO2 elimination below that of $CO_2$ production by the body. The circuit can include a customizable re-breathing circuit whose dead space is adjustable based on an individual's weight and estimated tidal volume, and desired or optimized level of hypercapnia (a $pCO_2$ rise of 2 or more mmHg above baseline levels would be optimum). The mask or vessel can incorporate one or several dead space channels or tubes that provide an inhale and exhale pathway that superimpose each other and thereby create mixing of inspired and expired gases. Alternatively, a source of fresh gas, potentially containing $CO_2$ can be supplemented when capnography (measurement of exhaled end-tidal $CO_2$), if utilized, so indicates. A re-breathing respiratory circuit may have one or more of the following: a mask or collecting vessel which has one or multiple channels or tubes whose length or volume is rapidly adjustable to regulate the amount of dead space that an individual will re-breath for the express purpose of raising or modulating their local $CO_2$ level within their blood stream. The circuit may also contain a physiologically insignificant amount of $CO_2$ in communication with a valve to be delivered to the patient, a fresh gas reservoir in communication with the source of fresh gas flow for receiving excess fresh gas not breathed by the patient, and a reserve gas supply containing $CO_2$ in communication with the exit port through the valve. Alternatively, a non-rebreathing circuit can be comprised of one or more of the following: a non-rebreathing valve preventing gas exhaled from the subject flowing into the circuit, a fresh gas source operative to supply a fresh gas containing physiologically insignificant amount of carbon dioxide to the subject through the non-rebreathing valve, and a reserved gas source operative to supply a reserved gas having a predetermined partial pressure of carbon dioxide to the subject through the non-rebreathing valve. These respiratory circuits can also be used to enable organisms to recover more quickly from vapor anesthetic administration, or poisoning with carbon monoxide, methanol, ethanol, or other volatile hydrocarbons. The circuit and method of treatment with 100% oxygen in the fresh gas and $CO_2$ in oxygen in the reserve gas may also be used to reduce nitrogen levels in the body. These additional uses may require higher concentrations of oxygen than ambient air. In this case, the fresh gas could contain 100% oxygen and the reserve gas would contain 0.04-100% $CO_2$; although simply maintaining a higher $pCO_2$ is all that is needed to improve outcomes in carbon monoxide poisoning.

Venous blood returns to the heart from the muscles and organs partially depleted of oxygen and containing a full complement of carbon dioxide. Blood from various parts of the body is mixed in the heart (mixed venous blood) and pumped into the lungs via the pulmonary artery. In the lungs, the blood vessels break up into a net of small capillary vessels surrounding tiny lung sacs (alveoli). The vessels surrounding the alveoli provide a large surface area for the exchange of gases by diffusion along their concentration gradients. After a breath of air is inhaled into the lungs, it dilutes the $CO_2$ that remains in the alveoli at the end of exhalation. A concentration gradient is then established between the partial pressure of $CO_2$ ($pCO_2$) in the mixed venous blood ($pvCO_2$) arriving at the alveoli and the alveolar $pCO_2$. The $CO_2$ diffuses into the alveoli from the mixed venous blood from the beginning of inspiration (at which time the concentration gradient for $CO_2$ is established) until equilibrium is reached between the $pCO_2$ in blood from the pulmonary artery and the $pCO_2$ in the alveoli at some time during breath. The blood then returns to the heart via the pulmonary veins and is pumped into the arterial system by the left ventricle of the heart. The $pCO_2$ in the arterial blood, termed arterial $pCO_2$ ($p_ACO_2$), is then the same as was in equilibrium with the alveoli. When the subject exhales, the end of his exhalation is considered to have come from the alveoli and thus reflects the equilibrium $CO_2$ concentration between the capillaries and the alveoli. The $pCO_2$ in this gas is the end-tidal $pCO_2$ ($p_{ET}CO_2$). The arterial blood also has a $pCO_2$ equal to the $pCO_2$ at equilibrium between the capillaries and alveoli.

With each exhaled breath some $CO_2$ is eliminated and with each inhalation, fresh air containing minimal $CO_2$ (presently 0.04%) is inhaled and dilutes the residual equilibrated alveolar $pCO_2$, establishing a new gradient for $CO_2$ to diffuse out of the mixed venous blood into the alveoli. The rate of breathing, or ventilation ($V_E$), usually expressed in L/min, is exactly that required to eliminate the $CO_2$ brought to the lungs and establish an equilibrium $p_{ET}$ $CO_2$ and $p_ACO_2$ of approximately 40 mmHg (in normal humans). When one produces more $CO_2$ (e.g. as a result of fever or exercise), more $CO_2$ is carried to the lungs and one then has to breathe harder to wash out the extra $CO_2$ from the alveoli, and thus maintain the same equilibrium $p_ACO_2$, but if the $CO_2$ production stays normal, and one hyperventilates, then excess $CO_2$ is washed out of the alveoli and the $p_ACO_2$ falls.

There are many scenarios in which we wish the inspired $CO_2$ to be greater than that which would normally come about physiologically. This heightened state of $CO_2$ in the system has many protective benefits but certainly one would not want to allow the increase in $CO_2$ to rise to dangerous levels.

One way to contribute to the $pCO_2$ levels of the organism can be by the delivery of one or more medicaments that are known to alter pH of the organism such as carbonic anhydrase inhibitors. Some examples of carbonic anhydrase inhibitors are Topiramate, Methazolamide, Dorzolamide or Acetazolamide. Carbonic anhydrase inhibitors can act as mild diuretics by reducing NaCl and bicarbonate reabsorption in the proximal tubule of the kidney. The bicarbonaturia will thus produce a metabolic acidosis. This mild acidosis has many potential benefits in mitigating SLOSH as described within. Anticipated acidic pH changes that would prove beneficial would be between about 7.30 and 7.40.

Another embodiment of elevating $pCO_2$ in the body of an organism can be a breathing circuit that maintains an elevated $pCO_2$. A circuit can maintain an estimated yet elevated end tidal $pCO_2$ by interposing one or more channels or tubes through which the individual breathes that causes a re-breathing of their previous inhaled or exhaled breath. These channels allow a mixing of inhaled ambient gas and exhaled alveolar gas. The optimal amount of gas re-breathed can be determined by estimating the individual's weight in kilograms and multiplying it by a factor, such as 7, to arrive at an estimated tidal volume in $cm^3$. In one embodiment a third of this volume can be added to the breathing circuit as dead space. This volume determines the predicted level of end tidal $CO_2$ to which the device will equilibrate. Alternatively a secondary source of $CO_2$ could be interposed to rapidly, and on demand, increase the percentage of inspired $CO_2$. Several paper or thin walled tubes or channels can extend away from the enclosed mouth and nose portion of the device and/or several regions can be placed sequentially along the channels or tubing as perforations or weakening points so as the individual will be able to tear, cut, or break off a predetermined amount of the tubing and thus precisely alter the remaining dead space of the circuit. Demarcations and identifiers placed along the channels/tubing can help the individual decide at which perforation or weakened zone to tear, cut, or remove. Again, these can be determined as follows: Tidal volume can be estimated by measuring one's weight in kilograms and multiplying by 7, the result would be in $cm^3$ of tidal volume. To determine the amount of dead space to add to the outflow tract of the mask, one need only take the resultant tidal volume and add a corresponding percentage of the tidal volume (say 33%) to the outflow tract of the mask. Each incremental increase in dead space added to the outflow tract would cause an incremental increase in final $pCO_2$. For example, if the weight of the individual is 120 kg then the estimated tidal volume would be 840 $cm^3$. We would want the individual to re-breath a portion of that tidal volume equating to 33% of this which equals 277 $cm^3$. This added volume of dead space would be expected to increase the $pCO_2$ by approximately 7-8 mmHg.

In addition to the adjustable dead space, monitoring the end tidal $CO_2$ and driving the export valve to open or close to alter the source of the next inspired breath may be utilized in settings whereby precise knowledge of end tidal $CO_2$ may be required. For example if an end tidal $CO_2$ desired range is 45 mmHg, then upon noting the end tidal $CO_2$ being only 35 mmHg, the valve would be directed to close requiring the individual to take the next breath from the adjustable dead space reservoir/tubing that a previous breath had been collected into. This expiration typically has 4-5% $CO_2$ within it allowing a greater inspired $CO_2$ on the next breath. A reservoir can act as a buffer to store extra $CO_2$ gas. Even when ventilation increases, the subject breaths the accumulated elevate $CO_2$ gas allowing $pCO_2$ to rise to the desired level. A circuit to maintain normal $CO_2$ can include a non-rebreathing valve, a source of fresh gas, a fresh gas reservoir and a source of gas to be inhaled, such as from the increased dead space region or a reservoir of higher concentration of $CO_2$.

The method of controlling $pCO_2$ in a patient at a predetermined desired level can be provided comprising a breathing circuit/mask which is capable of increasing the CO2 to enable an increase in cerebral blood flow and resultant cerebral blood pressure. With increased cerebral blood flow, cerebral blood velocity, and intracranial pressure there remains less space for intracranial tissues to move in relation to each other, thus brain pulsitility and SLOSH is diminished. This would require minimizing compressibility at air/fluid/tissue junctures. Although brain tissue is thought to be incompressible and fluid/blood is also relatively incompressible, the fluids are able to escape through the vessels and allow to and fro movement within the cranium and thus absorption of blast wave energies. If either the elevated $CO_2$ has been triggered with a resultant increase in cerebral blood flow and/or there has been increased intracranial pressure by any means before a traumatic event, the brain and its components would be less prone to slosh around within the cranium and in relation to each individual component (thus better approximating elastic collisions). This is not unlike seat-belting a passenger inside an automobile. Further, if TBI were to occur despite the above restraining effects of the increased cerebral blood flow, an elevated $CO_2$ would even serve to optimize the healing environment of the brain tissue itself by reducing the systemic inflammatory response and maximizing flow of oxygen rich hemoglobin which is more capable of delivering its oxygen due to high levels of $CO_2$ through maximizing the oxy-hemoglobin dissociation curve.

SLOSH absorption may also be reduced by reversibly increasing pressure or volume within the organs or cells of the organism. The intracranial volume and pressure can be reversibly increased by a device that reduces the flow of one or more outflow vessels of the cranium of said organism. One embodiment of such a device would compress the outflow vessels enough to cause an increase in venous resistance (approximately 15 mm Hg), yet not surpass arterial pressure of approximately 80 mmHg. Intracranial volume can also be reversibly increased by increasing the pCO2 in the arterial blood or by the delivery of one or more medicaments to facilitate an increase in intracranial volume or pressure including but not limited to Minocycline, insulin-like growth factor 1, Provera, and Vitamin A.

The human erythrocyte is very distensible and, as such, is particularly capable of absorbing energies imparted into it by suffering inelastic collisions. Mathematical analysis of Newton's Cradle shows that inelastic collisions absorb energy as heat and kinetic energy whereas elastic collisions serve to allow the forces to pass through without imparting as much energy. However, triggering an increase in $pCO_2$ in the blood and serum (resulting in erythrocytes pumping the $CO_2$ into the cytoplasm), can serve to cause nearly an immediate increase in bicarbonate created within the erythrocyte creating an osmotic swelling of fluid into the cell and reducing SLOSH absorption. Further, the walls of erythrocytes that have been exposed to higher levels of $CO_2$ have been shown to be less distensible; and also if swollen, they should facilitate more elastic collisions when forces are imparted into them. Even after the mechanism that supplies extra $CO_2$ has been removed, it will take hours for the cells to equilibrate back to pre-hypercapnia levels. This would further serve to reduce force impartation into the brain or any erythrocyte perfused structures. The reversible swelling of the cells and the altered red cell membrane's distensibility would also serve to mildly reduce the shear thinning capability that blood typically exhibits and again, this would serve to better approximate elastic collisions when forces are imparted.

In addition to increasing the volume within the cell one can also reversibly alter the vascular, molecular, or cell wall configuration within the organism to reduce SLOSH energy absorption. The configuration of the cell wall can be reversibly altered to increase membrane stability and decrease membrane fluidity. The addition of one or more of DHA and Magnesium oxide can be used to alter erythrocyte cell wall configuration. Typical DHA supplementations would be in the order of 50-1000 mg orally a day and MgO of 50-1000 mg orally a day. The configuration of hemoglobin can also be reversibly altered by altering one or more of pH (to a pH of about 7.0 to 7.5), $pCO_2$ (to $pCO_2$ of about 25 to 80 mmHg) or blood levels of 2,3-Bisphosphoglycerate (to about 6.0 to 1000 μmol/mL) within the organism to decrease hemoglobin elasticity and fluidity. 2,3-Bisphosphoglycerate levels may be increased by methods such as phosphate loading.

Another embodiment can be a compression device to reduce the likelihood of energy absorption to the brain through raising intracranial and intra ocular volume and pressure by applying pressure to the outflow vasculature and/or cerebral spinal fluid of the brain. The result would be an increase in the structure's coefficient of restitution (r) by attaching a cinch or collar around the neck of the individual or organism. The compression device can be of any design including, but not limited to, a band or cord. Such a compression device could be worn preferably before, in anticipation of and during events with SLOSH and traumatic brain injury risks.

Safely and reversibly increasing cerebral blood volume by any amount up to 10 $cm^3$ and pressure by any amount up to 70 mmHg would serve to fill up the compliance of the cerebral vascular tree and thus reduce the ability to absorb external energies through SLOSH energy absorption. "With the application of measured pressure to the neck, the cranial blood volume increases rapidly and plateaus at a new higher level. Moyer et al. reported that cerebral arterial blood flow was not affected by obstructing the venous outflow of blood from the brain."[1] "The blood volume venous pressure relationship shows a diminishing increase in volume with each increment of neck pressure over the range 40 to 70 mm of mercury. It is of interest that the cranial blood volume increases from 10 to 30 percent (with this neck pressure)."[2] The cerebral spinal fluid pressure responds on compression of the individual jugular veins. "The average rise was 48 percent."[3] Jugular compression increases cerebral blood flow to a new plateau in as little as 0.5 seconds.[4,5] This degree of cranial blood volume and pressure increase would be very beneficial in SLOSH mitigation. Although lesser cranial pressure and volume increases may still have beneficial effects, an increase of 3 $cm^3$ volume and 5 mmHg is a baseline goal. However, if pressure is distributed along the length of the veins, much less pressure, for example, as little as 5-10 mmHg is sufficient to increase flow resistance in the veins.

Further, safety of such a procedure of venous compression is quite abundant in the literature as it mirrors the 100 year old Quenkenstadt Maneuver. In this maneuver, "the compression of the neck does not interfere with arterial flow into the cranium. Although the venous jugular flow beneath the pressure cuff may be temporarily halted, the venous outflow from the cranium is never completely stopped, particularly from the anastomosis between the spinal vein and the basilar plexus and occipital sinuses which are incompressible."[6,7] In fact, there was no correlation between Electroencephalographic (EEG) changes or changes in systolic arterial blood pressure occurring during jugular compression.[8] Thus, neck compression of up to 70 mmHg does not affect cardiac output, arteriolar blood pressure, pulse rate, or urine flow.

The compression device may be of any material including but not limited to elastic materials. Elastic materials can be any material which when stretched will attempt to return to the natural state and can include one or more of textiles, films (wovens, non-wovens and nettings), foams and rubber (synthetics and natural), polychloroprene (e.g. Neoprene), elastane and other polyurethane-polyurea copolymerss (e.g. Spandex, Lycra), fleece, warp knits or narrow elastic fabrics, raschel, tricot, milanese knits, satin, twill, nylon, cotton tweed, yarns, rayon, polyester, leather, canvas, polyurethane, rubberized materials, elastomers, and vinyl. There are also a number of elastic materials which are breathable or moisture wicking which may be preferable during extended wearing periods or wearing during periods of exercise. In addition the compression device could be partially constructed, coated, or constructed of one or more protecting materials such as Kevlar (para-aramid synthetic fibers), Dyneema (ultra-high-molecular-weight polyethylene), ceramics, or shear thickening fluids.

The device may encompass circumferentially, the entire neck or just partially around the neck, yet still providing partial or total occlusion of one or more of the outflow vessels on the neck, specifically, but not limited to the internal and external jugular veins, the vertebral veins, and the cerebral spinal circulation. The device may encompass horizontally, the entire neck or just partially up and down the neck.

The width of the compression device may range from a mere thread (at a fraction of an inch) to whatever the length of the exposed neck (up to 12 inches in humans or greater in other creatures), the length may range from 6 to 36 inches to circumnavigate the neck. The thickness of said device could range from a film being only a fraction of a millimeter to a maximum of that which might be cumbersome yet keeps ones neck warm such as 2-3 inches.

One embodiment of the compression device may be preformed for the user in a circular construct. This one size fits all style can have a cinch of sorts that allows one to conform the device to any neck size. Alternatively the compression device may have a first and second end which is connected by a fastener. A fastener may be a hook and ladder attachment, a snap, a button or any of a number of attachment mechanisms that would be known to one skilled in the art. A compression device with a fastener could have a breakaway release mechanism whereby the device can break open or apart at a predetermined force to prevent the collar from inadvertently being snagged or compressing too tightly. One quick release or automatic release embodiment would be the applying of small amounts of hook and ladder attachments within the circumferential ring which would shear apart upon too much force being applied to the compression device. Another embodiment of the device could fasten such that the user would be able to pull one end of the collar (like a choker collar for a dog) and the force exerted by the user effectually decreases the length or circumference of the device. When the desired neck compression is no longer needed (such as between football plays) the user could then release the compression by a second gentle tug or by a separate release mechanism also positioned on the device.

The compression device may have one or more protuberances, or otherwise not be of consistent thickness or width. One such embodiment may have thicker protruding regions to be aligned with the internal jugular veins to preferentially compress these veins as the collar is tightened. Another embodiment may utilized inflatable protuberances as further described below.

The compression device may also have one or more monitoring, recording, and/or communicating devices attached or embedded. One such embodiment of the invention would be to embed a transceiver and/or receiver to allow communications between soldiers on a battlefield or even between coaches and players. Further, cardiac monitors could include heart rate or plethismography monitors that could provide real time evaluation of cardiophysiology while the compression device is in place. The compression device can also have a pocket or pouch attached depending on the height of the compression device used. Certainly, advertising can be imprinted or emblazoned onto the device. One such embodiment of the invention would have a wider segment of the collar positioned at the back of the neck on which to print a commercial design or brand name.

One other means of restricting bloodflow within the neck vasculature would be to incorporate one or more segments of inflatable bladders within the collar to alter the circumference or pressure the collar is exerting. One such embodiment could utilize a bulb pump placed in connection to the bladders whereby the user would compress the bulb one or multiple times until the desired pressure of air or fluid is retained within the bladder of the collar. Another embodiment may utilize pressurized gas or fluid which is connected to the bladders. Another embodiment would have a pressure release valve in communication with the bladders such that once a predetermined pressure is reached within the bladder, any successive pumping actions would merely divert the air or fluid pressure to the ambient air or the pump itself would simply no longer inflate (an existing correlate example would be the historical "Reebok Pump"). An embodiment with a pressure release valve could prevent overinflation of bladders and allow for a very precise degree of pressure delivery to the vasculature.

These terms and specifications, including the examples, serve to describe the invention by example and not to limit the invention. It is expected that others will perceive differences, which, while differing from the forgoing, do not depart from the scope of the invention herein described and claimed. In particular, any of the function elements described herein may be replaced by any other known element having an equivalent function.

[1] Moyer, J. H., Miller, S. I. and Snyder, H., *Effect of Increased Jugular Pressure on Cerebral Hemodynamics*, I. Appi. Physiol. 7:245, 1954

[2] *The Elasticity of the Cranial Blood Pool*, Masami Kitano, M.D., William H. Oldendorf, M.D.:C and Benedict Cassen, Ph.D., J. of Nuclear Medicine 5:613-625, 1964

[3] *Observations on the C.S.F Pressure during Compression of the Jugular Veins*, D. A. J. Tyrrell, Postgrad. Med. J. 1951; 27; 394-395

[4] *The Elasticity of the Cranial Blood Pool*, Masami Kitano, M.D., William H. Oldendorf, M.D.:C and Benedict Cassen, Ph.D., J, of Nuclear Medicine 5:616, 1964

[5] *A Cinemyelographic Study of Cerebrofluid Dynamics*, Amer. J. of Roent., Gilland et al. 106 (2): 369 (1969)

[6] Batson, O. V., *Anatomical Problems Concerned in the Study of Cerebral Blood Flow*. Fed. Proc. 3:139, 1944

[7] Gregg, D. E. and Shipley, R. E, *Experimental Approaches to the Study of the Cerebral Circulation*, Fed. Proc. 3:144, 1944.

[8] *Changes in the electroencephalogram and in systemic blood pressure associated with carotid compression*, Fernando Tones, M.D. and Anna Ellington, M.D., Neurology 1970; 20:1077

What is claimed is:

1. A method for reducing or preventing traumatic brain injury in a human subject comprising applying an externally-applied pressure of about 15 mm Hg to about 80 mm Hg to one or more outflow vessels of the cranium prior to and during a traumatic event.

2. The method of claim 1, wherein the pressure is applied to two or more outflow vessels of the cranium.

3. The method of claim 2, wherein the two or more outflow vessels comprises an internal jugular vein.

4. The method of claim 2, wherein the two or more outflow vessels comprises an external jugular vein.

5. The method of claim 1, wherein the one or more outflow vessels comprises an internal jugular vein.

6. The method of claim 1, wherein the one or more outflow vessels comprises an external jugular vein.

7. The method of claim 1, wherein the pressure is applied by a device worn about the neck of the subject, the device comprising a collar having one or more inwardly-directed structures positioned to partially or totally occlude the one or more outflow vessels of the cranium.

8. The method of claim 7, wherein the one or more outflow vessels comprises an internal jugular vein.

9. The method of claim 7, wherein the one or more outflow vessels comprises an external jugular vein.

10. The method of claim 7, wherein the device comprises two or more inwardly-directed structures positioned to partially or totally occlude the two or more outflow vessels of the cranium.

11. The method of claim 7, wherein the collar is sized to fully encircle the neck of the subject.

12. The method of claim 11, wherein the collar further comprises a breakaway release mechanism.

13. The method of claim 7, wherein the collar is sized to partially encircle the neck of the subject.

14. The method of claim 7, wherein the one or more inwardly-directed structures are non-inflatable.

15. The method of claim 7, wherein the one or more inwardly-directed structures are inflatable.

16. The method of claim 15, wherein the collar further comprises a pressure release valve.

* * * * *